United States Patent [19]
Markov et al.

[11] Patent Number: 5,944,020
[45] Date of Patent: Aug. 31, 1999

[54] USE OF FRUCTOSE-1 6-DIPHOSPHATE AS AN INOTROPE DRUG AFTER CARDIOPULMONARY BYPASS SURGERY

[75] Inventors: Angel K. Markov, Jackson, Miss.; Paul J. Marangos, Encinitas; Anthony W. Fox, Rancho LaCosta, both of Calif.

[73] Assignee: Cypros Pharmaceutical Corp., Carlsbad, Calif.

[21] Appl. No.: 08/943,836

[22] Filed: Oct. 3, 1997

Related U.S. Application Data

[63] Continuation-in-part of application No. 08/805,282, Feb. 25, 1997, abandoned.

[51] Int. Cl.$^6$ .................................................. A61B 19/00
[52] U.S. Cl. ............................................. 128/898; 514/23
[58] Field of Search ................................ 128/898; 514/23, 514/340; 536/117; 435/2, 105, 188, 194, 18; 424/643, 646, 680, 682, 94.1–94.5

[56] References Cited

U.S. PATENT DOCUMENTS

| | | |
|---|---|---|
| 4,530,902 | 7/1985 | Perri et al. . |
| 4,546,095 | 10/1985 | Markov . |
| 4,575,549 | 3/1986 | Diana et al. . |
| 4,703,040 | 10/1987 | Markov . |
| 4,870,057 | 9/1989 | Chiapparelli et al. . |
| 5,039,665 | 8/1991 | Markov . |
| 5,094,947 | 3/1992 | Nakajima et al. . |
| 5,434,255 | 7/1995 | Katayama et al. . |
| 5,506,210 | 4/1996 | Parish et al. . |
| 5,516,526 | 5/1996 | da la Torre . |
| 5,571,906 | 11/1996 | Ceccarelli et al. . |
| 5,731,291 | 3/1998 | Sullivan et al. . |

FOREIGN PATENT DOCUMENTS

| | | |
|---|---|---|
| 108615 | 7/1994 | China . |
| 1089616 | 7/1994 | China . |
| 1089654 | 7/1994 | China . |
| 3323850 | 1/1985 | Germany . |

OTHER PUBLICATIONS

Angelos, M.G., et al, "Fructose–1,6–diphosphate fails to limit early myocardial infarction size in a canine model," *Ann. Emerg. Med.* 22: 171–177 (1993).

Brunswick, R., et al, "Preservation of myocardium by infusion of fructose diphosphate following coronary occlusion," abstract, *Am J Cardiol* 49: 1008 (1982).

Cargnoni, A., et al, "Role of timing of administration in the cardioprotective effect of fructose–1,6–bisphosphate," *Cardiovasc Drugs Ther* 6: 209–17 (1992).

Conti, V.R., et al, "Metabolic and functional effects of carbohydrate substrate with single–dose and multiple–dose potassium cardioplegia," *Ann. Thoracic Surg.* 36: 320–327 (1983).

(List continued on next page.)

*Primary Examiner*—Mickey Yu
*Assistant Examiner*—Kelly O'Hara
*Attorney, Agent, or Firm*—Patrick D. Kelly

[57] ABSTRACT

When fructose-1,6-diphosphate (FDP) is used as an inotropic drug in patients who have undergone surgery involving cardiopulmonary bypass, it can increase the pumping strength of a struggling heart, without increasing the heartbeat rate. As such, FDP can reduce the dosages of (and in some some cases eliminate the need for) other inotropic drugs such as dobutamine, epinephrin, or amrinone lactate, which have undesired and potentially dangerous side effects, mainly involving increasing the heartbeat rate, which imposes substantial additional stresses on hearts that are struggling to regain strength after cardiopulmonary bypass surgery.

6 Claims, 4 Drawing Sheets

OTHER PUBLICATIONS

Eddy, L.J., et al, "Lack of a direct metabolic effect of fructose, 1,6–diphosphate in ischemic myocardium," *Am J Physiol 241*: H576–83 (1995).

"Esafosfina" sales brochure (Biomedica Foscama; Ferentino, Italy).

Farias, L.A., et al, "Effects of fructose–1,6–diphosphate, glucose and saline on cardiac resuscitation," *Anesthesiology 65*: 595–601 (1986).

Granot, H., et al, "Successful treatment of irreversible hemorrhagic shock in dogs with fructose–1,6 diphosphate and dichloroacetate," *Circ Shock* 163–73 (1985).

Haasinen, I.E., et al, "Mechanism of the effect of exogenous FDP on myocardial energy metabolism," *Circulation 83*: 584–593 (1991).

Lazzarino G., et al, "Protective effects of exogenously administered fructose–1,6–diphosphate from ischemia reperfusion damage induced on isolated rat heart," *Ital J Biochem 38*: 251A–253A (1989).

Lazzarino, G., et al, "Ischemia and reperfusion: effect of fructose–1,6–bisphosphate," *Free Radic Res Commun 16*: 325–39 (1992).

Marchionni, N., et al, "Hemodynamic and electrocardio-graphic effects of fructose–1,6–diphosphate in acute myocardial infarction," *Am J Cardiol 56*: 266–269 (1985).

Markov, A.K., et al, "Prevention of arrhythmias with fructose diphosphate in acute myocardial ischemia," abstract, *Circulation 62*: III–143 (1980).

Markov, A.K., et al, "Hemodynamic, electrocardiographic, and metabolic effects of fructose diphosphate on acute myocardial ischemia," *Am Heart J 100*: 639–46 (1980).

Markov, A.K., "Hemodynamics and metabolic effects of fructose 1–6 diphosphate in ischemia and shock—experimental and clinical observations," *Ann Emerg Med 15*: 1470–7 (1986).

Markov, A.K., et al, "Increasing survival of dogs subjected to hemorrhagic shock by administration of fructose 1–6 diphosphate," *Surgery 102*: 515–27 (1987).

Markov, A.K., et al, "Improvement of hemodynamics and pulmonary function following fructose 1–6 diphosphate administration in ARDS patients," *Microcirculation 1*: 173–178 (1987).

Pasque, M.K., et a, "Metabolic intervention to affect myocardial recovery following ischemia," *Annals of Surgery 200*: 1–12 (1984).

Sernov, L.N., et al, "The characteristics of the cardioprotective action of fructose–1,6–diphosphate," *Biull Eksp Biol Med 111*:172–3 (1991) (abstract).

Sernov, L.N., et al, "The antiacidotic and cardio–protective effects of fructose–1,6–diphosphate and dehydroascorbic acid," *Farmakol Toksikol 54*:24–26 (1991) (abstract).

Sernov, L.N., et al, "A comparative evaluation of the cardioprotective and antianginal actions of energy–providing agents," *Eksp Klin Farmakol 55*:13–15 (1992) (abstract).

Stryer, L., *Biochemistry*, 2nd ed., pp. 266–267 (Freeman & Co., San Francisco, 1981).

Zhang, J.N., et al, "Protective effect of exogenous fructose–1,6–diphosphate in cardiogenic shock," *Cardiovasc Res 22*: 927–32 (1988).

Left ventricular function curves of patients undergoing coronary artery bypass surgery

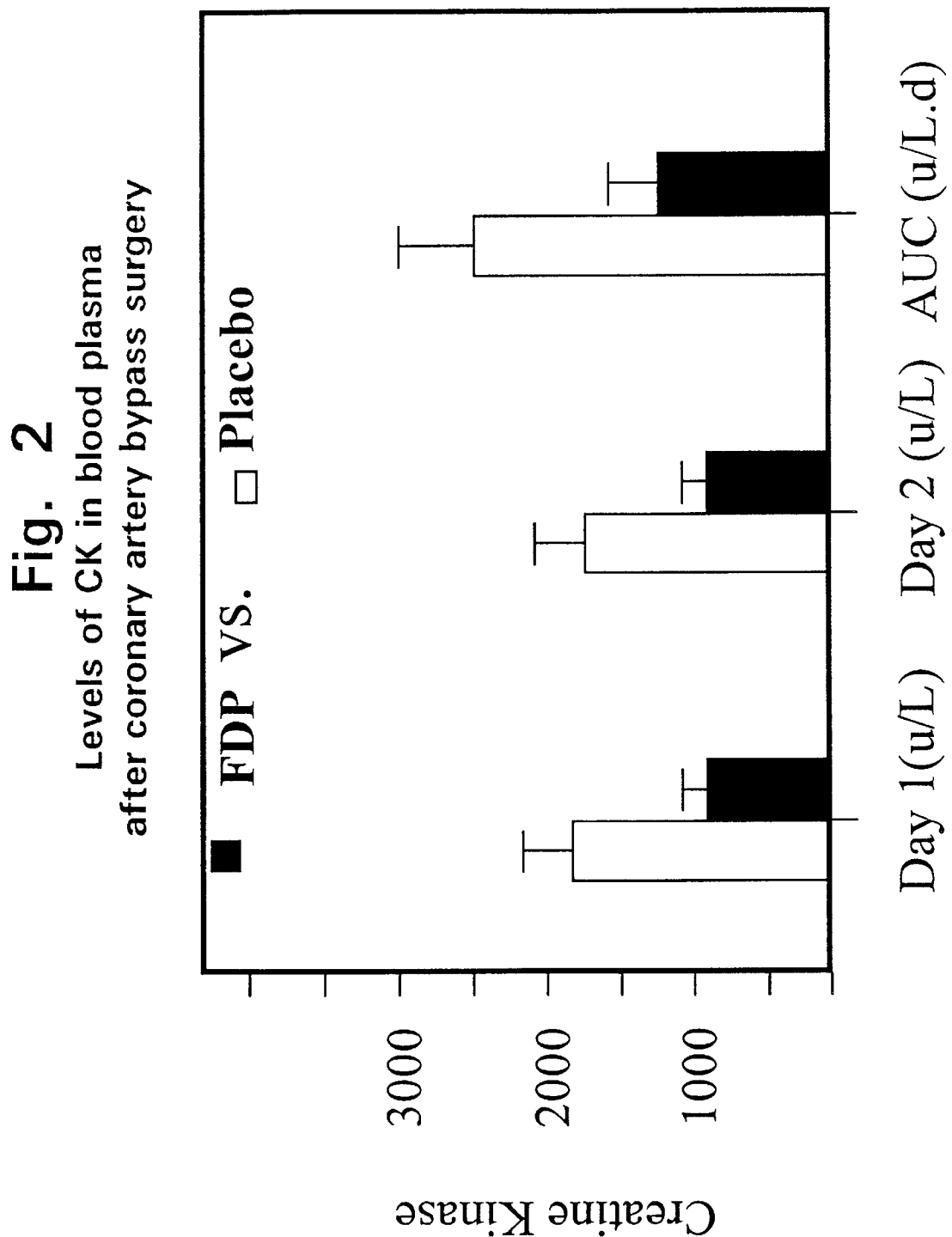

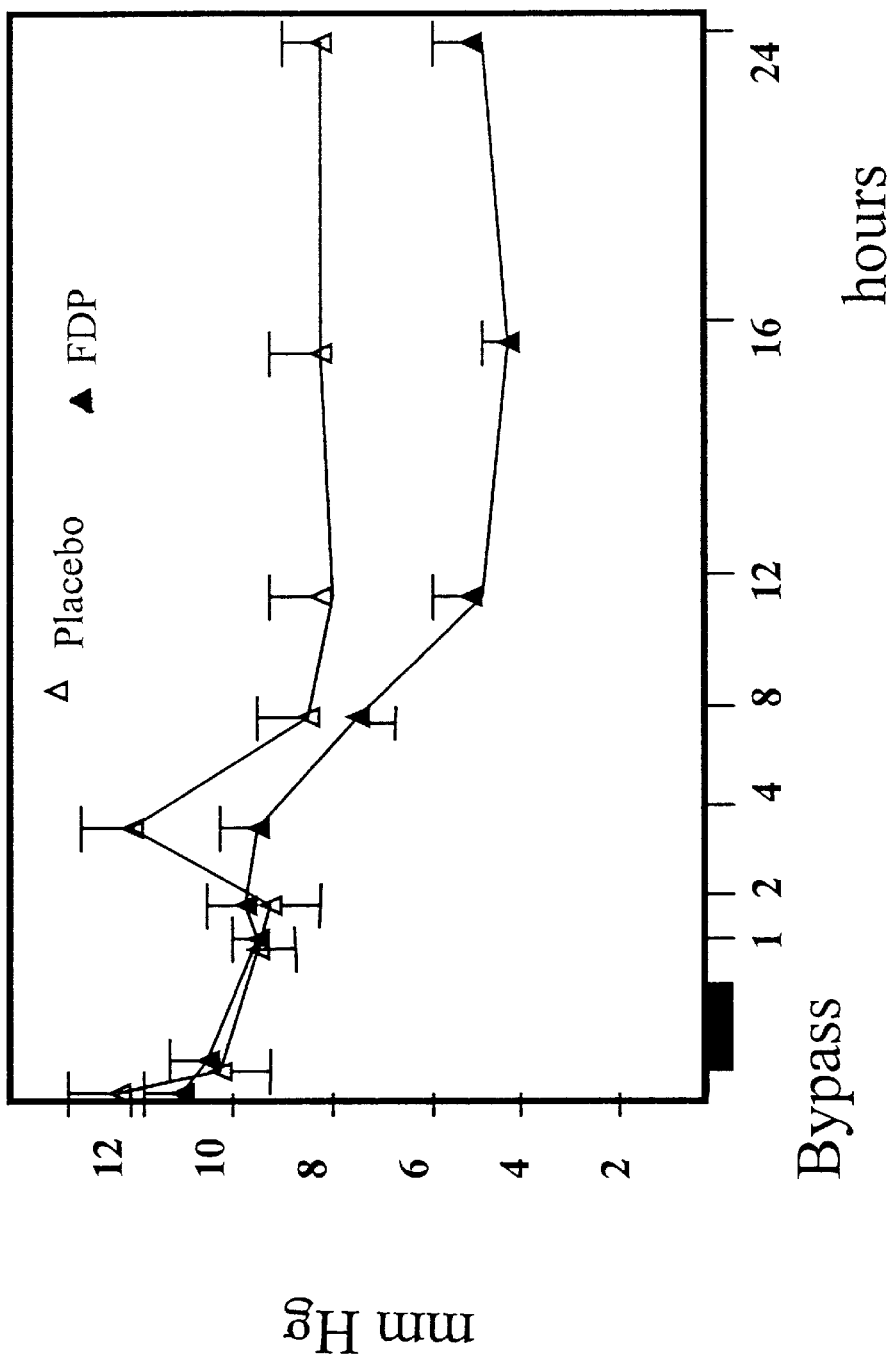

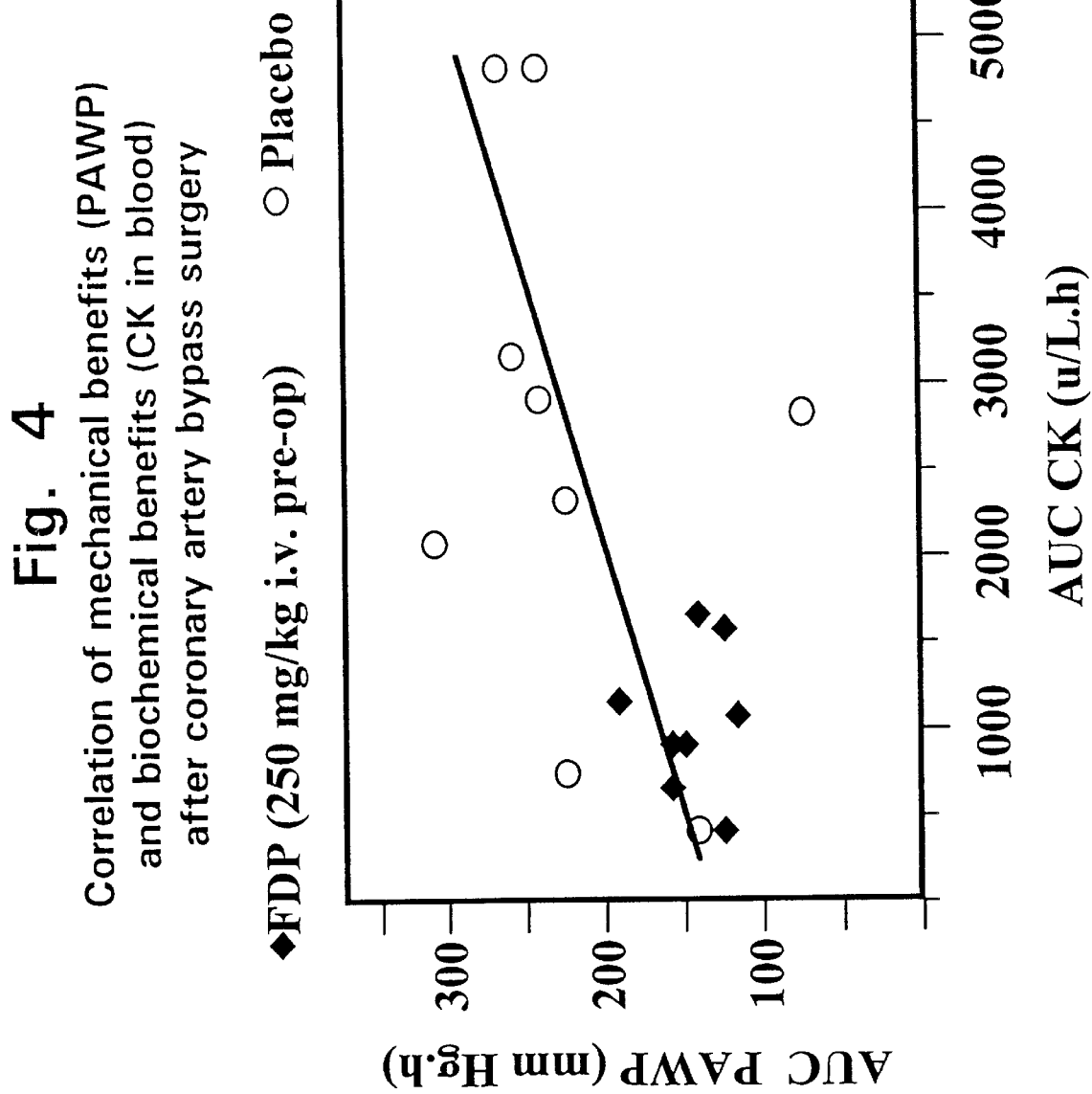

USE OF FRUCTOSE-1 6-DIPHOSPHATE AS AN INOTROPE DRUG AFTER CARDIOPULMONARY BYPASS SURGERY

RELATED APPLICATION

This application is a continuation-in-part of U.S. patent application Ser. No. 08/805,282, filed on Feb. 25, 1997 now abandoned.

BACKGROUND OF THE INVENTION

This invention relates to inotrope drugs, which can increase the strength of a heartbeat. Such drugs are often used after cardiac surgery, if a patient's heart is struggling to regain adequate strength after the patient has been taken off of a cardiopulmonary bypass machine.

Patients are often put on cardiopulmonary bypass (CPB) for heart surgery (including coronary artery bypass, heart valve repair or replacement, surgery to correct an arryhthmia, heart transplants, etc.), and, less frequently, for other types of surgery as well, including various types of pulmonary or brain surgery. The equipment and techniques involved in CPB surgery are described in numerous medical textbooks and articles, including *Surgery of the Chest* (Sabiston and Spencer, eds., Saunders Publ., Philadelphia) and *Cardiac Surgery* by Kirklin and Barrett-Boyes and various articles cited therein.

As is well-known to cardiac surgeons, some patients who undergo CPB surgery encounter serious difficulty in regaining a sufficiently strong and stable heartbeat when they are "weaned" from the CPB pumping machine. Such problems are especially common among elderly patients, and among patients who suffer from severe or prolonged heart disease. Various mechanical methods and equipment can be used to assist the heart, including implantation of a pacemaker to stabilize the frequency of a heartbeat, and, in extreme cases, temporary implantation of a so-called "left ventricular assist" (LVAD) pumping device.

Various drugs (generally referred to as "inotropes" or "cardiotonic" agents) are also widely used to stimulate the heart muscle and increase the strength of a heartbeat, after cardiac surgery. The most widely used inotrope drugs include digitalis glycosides (also called digoxins), various inotropic catecholamines, including epinephrin and norepinephrin (also called adrenaline and noradrenaline), dopamine, and dobutamine, and a drug called amrinone lactate.

All of these previously known inotrope drugs suffer from various risks, limitations, and adverse side effects, and they are not administered unless it becomes apparent in a specific patient that such drugs are needed to deal with a medical crisis. In general, they all interact directly with neuronal and/or hormonal receptors (primarily beta receptors, on heart cells), triggering various types of artificially-stimulated excitation of the activated cells and tissue. Therefore, such inotrope drugs alter and disrupt the desirable homeostatic balances and equilibria that a heart tries to maintain.

In particular, all previously known inotrope drugs have an undesirable and potentially dangerous side effect: they increase the rate of the heartbeat (the number of beats per minute). This imposes a severe form of stress on an already-stressed heart, and such drugs are dangerous to the point of lethal in substantial numbers of patients; even a slight overdose of a conventional inotrope can drive an already weakened cardiac surgery patient into cardiac failure and collapse.

By contrast, a better inotropic drug would increase the strength of the heartbeat (as measured by indices such as volume of blood output per heartbeat stroke), without increasing the heartbeat rate (i.e., without causing the heart to beat faster.

A second undesired and dangerous aspect of previously known inotrope drugs is that their useful effects diminish fairly quickly over time; within about 3 days, the efficacy of any of these drugs drops to about half of what it was when treatment commenced. This drop of efficacy involves a form of drug tolerance that is usually known as "tachyphylaxis". It is especially dangerous, because all beta receptor agonists (which includes nearly all of the inotropic catecholamines) share this property. In other words, if dopamine is used as an initial inotrope, during the first days when someone's heart is not beating adequately after CPB surgery, then it will not help the patient to switch to some other catecholamine or other beta agonist when the dopamine efficacy drops off.

Even if a conventional inotrope drug works exactly as hoped during the first day or two after surgery, it can leave the heart in a compromised position as it wears off. Inotrope drugs are heart stimulants, pure and simple. Accordingly, giving a weakened patient an inotrope drug, after cardiac surgery, is comparable to giving a stimulant such as amphetamine (commonly called "speed") to someone who is exhausted, due to overexertion combined with lack of adequate food. The stimulant may offer a quick fix; it may help the person deal with a specific short-lived demand or deadline.

However, after the stimulant wears off, the person will be even more exhausted, and depleted. His/her need to rest and recover will be even more severe than it was, before he or she took the stimulant drug. Stimulants which increase the heartbeat rate can actually induce (precipitate) hypoxia and ischemia, in tissue that is already starved for oxygen; using stimulant drugs to force the heart to beat faster, shortly after bypass surgery, is like forcing a person to run sprints, shortly after that person has suffered a near-drowning accident.

Unlike a person suffering from severe exhaustion, a heart cannot go to sleep so it can rest, recover, and regain strength. It must continue beating actively, even when the patient is resting or sleeping. Accordingly, it is difficult and dangerous to subject a heart to the type of "double-tired" exhaustion that results from using stimulant drugs to drive the heart harder and faster while it is trying to recover from a severe ordeal.

As noted, all of the previously known inotropic drugs work by artificially stimulating certain hormonal or neuronal receptors (mainly beta receptors) on the heart. By contrast, FDP (the inotropic drug discussed below) works by an entirely different mechanism. Instead of triggering abnormally high activity in heart muscle by stimulating hormonal or neuronal receptors, it provides a completely safe and healthy form of nutrition for the heart muscle. By way of analogy, providing FDP to a struggling heart is like giving a good, nutritious, healthy meal (rather than dangerous hunger-suppressing amphetamines) to a starving person. Rather than masking symptoms and leading to even more severe forms of exhaustion, a good, nutritious, and healthy meal can help a starving man regain his strength and restore a safe and stable balance, after he has suffered through a severe ordeal.

That is the goal, and the result, of this invention.

Furthermore, unlike previously known inotropes, such as adrenalin or norepinephrin, FDP does not increase the heartbeat rate to abnormally high levels. The tests done to date indicate that FDP no statistically significant effects on heartbeat rate. Instead, it merely strengthens the heart, so that the "hemodynamic performance" of the heart during each heartbeat is improved, as indicated by the various measures described below.

Measures of Heart Performance

There are several indices that can be measured and/or calculated to evaluate the strength and condition of a heart. These indices, along with their abbreviations and units of measurement, are listed below. In all indices, LV refers to the left ventricle, while mm Hg is a pressure value, expressed as millimeters of a mercury column. These values can be measured and calculated as described in Grossman 1991.

CO—cardiac output, expressed as liters of blood pumped per minute.

CI—cardiac index, expressed as liters of blood pumped per minute, divided by the body surface area of the patient, in square meters.

SVI—stroke volume index, expressed as milliliters of blood pumped per heartbeat, divided by the body surface area of the patient, in square meters.

LVSP—left ventricular systolic pressure, expressed in mm Hg. This is a peak pressure generated during contraction of the left ventricle.

LVSWI—left ventricular stroke work index, expressed as grams-meters, divided by the body surface area of the patient in square meters.

LVEDP—left ventricular end diastolic pressure, expressed as mm Hg.

MAP—mean aortic pressure, expressed as mm Hg, indicates the pressure that contraction of the left ventricle is able to generate, averaged over an entire heartbeat.

PVR—pulmonary vascular resistance, expressed in dynes-seconds divided by $cm^5$.

SVR—systemic vascular resistance, expressed as dynes-seconds divided by $cm^5$.

MPAP—mean pulmonary artery pressure, expressed in mm Hg.

Fructose-1,6-Diphosphate (FDP)

Fructose-1,6-diphosphate (FDP) is a naturally occurring sugar-phosphate molecule, which is created and then quickly consumed as an intermediate during the series of reactions that make up glycolysis. As a short-lived intermediate that is quickly consumed, it normally is present in cells only at relatively low concentrations. It should be noted that some scientists refer to FDP as fructose-1,6-biphosphate, or fructose-1,6-bisphosphate.

The 1,6-isomer of fructose diphosphate, which contains phosphate groups bonded to the #1 and #6 carbon atoms of the fructose molecule, is the only isomer of interest herein. Other isomers (such as fructose-2,6-diphosphate) are not relevant herein, and are excluded from any references herein to FDP or fructose diphosphate.

Numerous medical and scientific articles have suggested that FDP might potentially be useful as a medical treatment for medical crises such as strokes, cardiac arrest, heart attack, suffocation, loss of blood due to injury, shooting, or stabbing, etc. Such articles include Markov et al 1980, 1986, and 1987, Brunswick et al 1982, Marchionni et al 1985, Farias et al 1986, Grandi et al 1988, Zhang et al 1988, Lazzarino et al 1989 and 1992, Janz et al 1991, Hassinen et al 1991, Cargnoni et al 1992, and Munger et al 1994. Relevant U.S. patents include U.S. Pat. Nos. 4,546,095 (Markov 1985), 4,703,040 (Markov 1987), and 4,757,052 (Markov 1988).

Despite all of these published articles and patents, which stretch back roughly 20 years, a high degree of skepticism and reluctance still exists regarding FDP use to treat ischemia or hypoxia. Except for a few small and very limited clinical trials, FDP simply is not used or prescribed by any practicing physicians, except possibly in a few foreign countries such as China and Italy.

The absence of actual use of FDP on patients is believed to be due to a number of factors, including the following:

(1) FDP is a diphosphate with a strong negative charge; accordingly, it is generally assumed by doctors and researchers that its highly-charged nature will prevent it from entering cells in substantial quantities. Since energy metabolism and glycolysis occur inside cells, it is generally assumed that FDP will not get to the relevant site in sufficient quantities to do any substantial good.

(2) It is also believed that FDP has a very short half-life in the blood, and will effectively disappear from the blood within a few minutes after injection or infusion.

(3) The amount of energy generated during glycolysis (i.e., the conversion of glucose to pyruvic acid) is only a small fraction of the energy generated by the aerobic (Krebs Cycle) oxidation of pyruvic acid to form carbon dioxide and water. Therefore, under conditions of tissue ischemia or hypoxia, where an oxygen deficit blocks aerobic conversion, it is generally assumed that FDP infusion would be insufficient to supplement ATP levels to a degree that can significantly aid cell survival.

(4) It is also generally assumed that under conditions of ischemia or hypoxia, where inadequate oxygen is present, an injection of FDP would likely lead to increases in lactic acid levels. This would be harmful, rather than beneficial.

(5) Contrary to the articles cited above, which report that FDP may have beneficial effects in certain types of lab tests, a number of other articles have reported that FDP had no beneficial effects in other studies. Examples of these negative articles include Eddy et al 1981, Pasque et al 1984, Tortosa et al 1993, and Angelos et al 1993.

For these and other reasons, it appears that little if any effort has been directed by the pharmaceutical industry toward developing FDP as a useful drug. Under the laws enforced by the U.S. Food and Drug Administration (and by comparable agencies in other countries, such as the Medicines Control Agency, in Great Britain), FDP cannot be sold in the United States for administration to human patients by physicians. With the possible exception of a few small clinical trials, FDP simply is not administered to any patients, on any sort of routine basis, regardless of how desperate their plight may be following a stroke, cardiac arrest, shooting, stabbing, etc.

Currently, there are only two known preparations of FDP which are commercially available anywhere in the world, other than research reagents that are sold in gram or milligram quantities by specialty chemical companies. One of these preparations is a non-sterile bulk powder, manufactured in Germany by Boehringer Mannheim. This material was purchased by the assignee (Cypros Pharmaceutical Corporation, of Carlsbad, Calif.) and used as a starting reagent to prepare the sterilized injectable formulations described herein.

The other commercially available FDP formulation is a lyophilized preparation that is manufactured in Italy by a company called Biochemica Foscama. To the best of the Applicant's knowledge and belief, it is manufactured by steps that including the following: (1) pouring a large batch of an aqueous mixture of FDP into a large, flat tray; (2) freezing the mixture and subjecting it to a vacuum, to remove the water, thereby creating a large solidified cake; (3) grinding or milling the large cake into small particles; (4)

loading the ground-up particles into small vials; and, (5) sealing the vials. This process is not well suited for creating a sterile preparation for injection into humans; a process that uses large machinery to handle and manipulate a large cake, pass it through a device which grinds it up into small particles, pass the particles through various routing and funnelling devices in order to load those particles into small vials, and then seal the vials, creates numerous risks which seriously jeopardize the sterility of the resulting final product.

It should also be noted that if non-sterile FDP is loaded into a sealed vial, it cannot be subsequently treated by a "terminal sterilization" process, such as autoclaving or ionizing radiation. Those types of terminal (post-sealing) sterilization treatments would seriously degrade the chemical quality of the FDP in the sealed vials.

In addition to the two FDP preparations that are currently available from companies in Germany and Italy, as discussed above, several other patents have been issued during the last few years which describe methods for synthesizing or purifying FDP. The synthesis methods usually involve microbes which will convert glucose into FDP, if provided with glucose and a phosphate donor under proper fermentation conditions; these include Chinese patent 1,089,654 A (Yin, 1994) and U.S. Pat. Nos. 4,530,902 (Perri et al 1985) and 5,094,947 (Nakajima et al, 1991). The purification patents usually involve ion exchange chromatography; see U.S. Pat. Nos. 4,575,549 (Diana et al, 1986; apparently equivalent to German patent DE 3,446,927) and 5,434,255 (Katayama et al, 1995; apparently equivalent to Japanese patent JP 05271269 A2) as well as Chinese patents 1,089, 615 A (Ying et al 1994) and 1,089,616 A (Ouyang et al 1994).

However, to the best of the Applicant's knowledge and belief, none of the recently developed methods for preparing FDP have yet culminated in any FDP preparations that are commercially available. Despite all of the published medical articles which stretch back roughly twenty years, a high degree of skepticism and reluctance still exists, regarding the medical use of FDP in humans. Except for a few very small and limited clinical trials, FDP simply is not used or prescribed by any practicing physicians, except possibly in a few foreign countries such as China and Italy.

Accordingly, one object of the subject invention is to provide a better cardiac inotrope for patients who are recovering from surgery which involved cardiopulmonary bypass. This improved and desired inotrope should strengthen and help stabilize the heartbeat, but it should not increase the heartbeat rate, and it should not have any other undesired side effects.

Another object of the subject invention is to disclose that FDP can be used as a safe and effective cardiac inotrope drug, for people emerging from surgery which required cardiopulmonary bypass.

Another object of the subject invention is to disclose that when FDP is used as a cardiac inotrope drug after surgery involving cardiopulmonary bypass, it provides a virtually ideal combination of desired activities coupled with an apparently complete absence of any undesired side effects.

These and other objects of the invention will become more apparent through the following summary, drawings, and description of the preferred embodiments.

SUMMARY OF THE INVENTION

This invention discloses that fructose-1,6-diphosphate (FDP) can be used, safely and effectively as an inotropic drug, in humans who have undergone surgery involving cardiopulmonary bypass. As a sugar-phosphate compound which has inotropic effects, FDP can increase the pumping strength of a struggling heart, without increasing the heartbeat rate. As such, if FDP is administered as a sole inotropic drug, it will be able, in at least some cases, to eliminate the need for other inotropic drugs (such as dobutamine, epinephrin, or amrinone lactate) which have undesired and potentially dangerous side effects.

Alternately, FDP also can be administered in combination with other inotropic drugs which cause an increase in heartbeat rate. When co-administered with such other drugs, FDP can reduce the dosages of the other inotropic drugs that are required to achieve the necessary effects. By reducing the required dosage of an HR-increasing inotrope, FDP can minimize any unwanted increase in heartbeat rate.

It is also disclosed herein that FDP has no known adverse effects, when used as an inotropic drug in patients who have undergone cardiac surgery. Accordingly, FDP can be administered safely in inotropic dosages, as a preventive measure, among any and all patients who are emerging from surgery involving cardiopulmonary bypass. Patients who do not need its inotropic effects will not be adversely affected by it, while patients who are likely to benefit from its inotropic effects can obtain maximal benefit if it is injected immediately after bypass is terminated, or at the first symptoms of heartbeat deficit.

BRIEF DESCRIPTION OF THE DRAWINGS

FIG. 2 shows that FDP caused a significant reduction in CK levels in circulating blood plasma (measured on the first and second post-operative days), compared to a placebo treatment, in patients who underwent cardiopulmonary bypass surgery.

FIG. 3 shows that FDP significantly helped patients regain a more normal left-side heart function, as measured by reduced elevations of pulmonary artery wedge pressure on the first post-operative day.

FIG. 4 is a graph which shows how the biochemical benefits of FDP (measured by CK levels in blood plasma), correlate with the mechanical and hemodynamic benefits of FDP (measured by reduced abnormalities in pressure values). This correlation is statistically significant, and it confirms that FDP provides both biochemical and hemodynamic benefits when administered before circulatory bypass begins.

DESCRIPTION OF THE PREFERRED EMBODIMENTS

Figure 1:
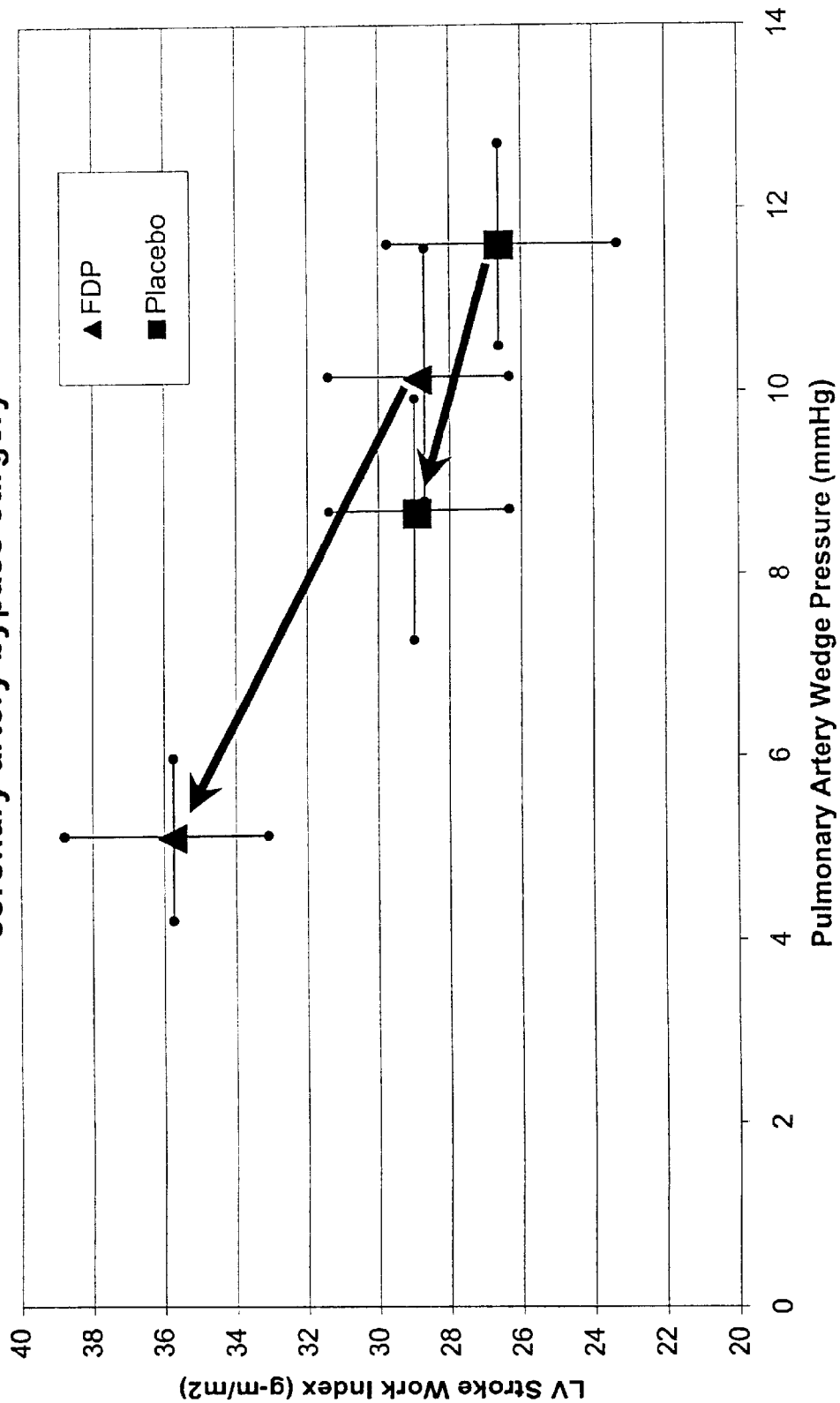
FIG. 1 shows that FDP caused a significant increase in the "left ventricular stroke work index" (LVSWI), compared to a placebo, in patients who underwent cardiopulmonary bypass surgery. It also shows that FDP helped reduce unwanted increases in "pulmonary artery wedge pressures" (PAWP values) after bypass surgery, compared to a placebo.

As summarized above, FDP can be used as a safe and effective inotropic drug, after surgery, to strengthen the heartbeats of patients who have been through cardiopulmonary bypass. When used in this manner, it can increase the strength of the heartbeat, as measured by indices such as cardiac output (CO; liters/minute), cardiac index (CI; liters/minute/$M^2$), and stroke volume index (SVI; ml/beat/$m^2$), without increasing the heartbeat rate (HR; beats/minute).

The ability to increase heartbeat strength, without increasing heartbeat rate, is a very valuable inotropic property of FDP, since increasing the heartbeat rate in a heart after CPB surgery can impose severe and potentially lethal stress and hypoxia on a heart that is already struggling to recover and regain strength after an ordeal.

The hemodynamic effects of intravenously administered FDP were compared in patients suffering from various types of coronary artery disease. Hemodynamic measurements were performed before and after administration of FDP, in two groups of patients: (1) patients with impaired left ventricular (LV) function, as indicated by LVEDP values of 12 mm Hg or higher (n=30); and (2) patients with normal LV function, as indicated by LVEDP values of less than 12 mm Hg (n=17). Various comparative traits of these two patient groups are provided in Table I.

In patients with impaired LV function, FDP treatment reduced LVEDP values from a pretreatment mean value of 22 mm Hg to a post-treatment value of 16.73 (standard error of the mean values, and statistical significance values, are provided in the tables). The cardiac index also increased, from 2.50 L/min/m$^2$ (pretreatment) to 2.81 (post-treatment). The LV stroke work index (LVSWI) values incresed from 31.7 gm-m/m$^2$ (pretreatment) to 40.3 (posttreatment). Pulmonary pressure and resistance declined, and systemic vascular resistance decreased, by virtue of increased cardiac output and unchanged arterial pressure.

Despite these highly significant increases in heartbeat strength and vigor in patients with impaired LV function, FDP caused no increase whatsoever in the heartbeat rates of the patients. Indeed, FDP treatment actually reduced the heartbeat rates in all treatment groups, presumably due to the various regulatory mechanisms that govern heartbeat; as the body is provided with an improved flow of blood due to increased heartbeat strength, the tissues of the body do not send out the various nerve impulses that indicate oxygen deficits, which cause the heartbeat rate to increase.

As noted above, the absence of any increase in heartbeat rate, despite the strong inotropic effects of FDP, is an exceptionally important and valuable result, since it means that the struggling hearts are not being stressed and forced to beat at abnormally high speeds, as caused by inotropic stimulants such as dobutamine or adrenaline.

In patients with normal baseline LVEDP (defined as having LVEDP values of less than 12 mm Hg; actual mean value was 5.06±0.27), FDP also decreased heart rate and systemic and pulmonary resistance, while LVEDP, mean aortic pressures, and pulmonary pressures were not significantly altered. FDP moderately increased cardiac output, stroke volume index, and LVSWI.

The lack of any adverse side effects in patients who do not need inotropic treatment is also very important. It indicates that (1) FDP can be administered safely to virtually anyone, and it will not lead to any undesired or disruptive side effects; (2) FDP can be administered safely at the earliest onset of any symptoms of cardiac distress following CPB surgery, to minimize the overall stress and strain that a heart must struggle with after CPB surgery; and (3) FDP can even be administered safely as a preventive measure to all patients who are emerging or recovering from CPB surgery, to reduce the risk that such patients will suffer from cardiac deficits and irregularities that would require treatment by strong and potentially harsh and dangerous drugs.

The detailed procedures used to gather these data are provided in Examples 1–3.

These specific tests involved administration of FDP before cardiac catheterization procedures, which were being used to diagnose a number of patients who were suffering from coronary artery disease. During these tests, the Inventor herein clearly observed the strong inotropic effects of FDP. However, because of the cellular and biochemical menchanisms involved, it is believed and anticipated that the same types of beneficial inotropic effects (i.e., increasing heartbeat strength and cardiac output without increasing heartbeat rate) will also occur if FDP is injected or infused into a patient after cardiopulmonary bypass surgery. If a patient is struggling with cardiac deficiencies that would otherwise require treatment with an inotropic catecholamine that increases heartbeat rate as an undesired side effect, injection or infusion with FDP appears to be highly advisable and may offer either (1) an effective alternative to inotropic catecholamine treatment, or (2) a means to reduce the dosage of (and ameliorate the increase in heartbeat rate caused by) an inotropic catecholamine.

In addition to the data in Examples 1–3, which were gathered from people who underwent diagnostic cardiac catheterization because they suffered from known or suspected coronary artery disease, an additional set of data is provided in Example 4, obtained during testing of FDP on patients who underwent open-chest surgery that involved cardiopulmonary bypass. As described in more detail in Example 4, these patients received coronary artery bypass grafting (CABG). Because of the initial design of the surgical tests, which were planned and designed before it was recognized that FDP would indeed function as an inotrope, these tests involved infusion of FDP into the patients prior to the commencement of bypass (usually during a 30-minute period prior to commencement of bypass). The resulting data clearly indicate, however, that FDP does indeed have inotropic properties in surgical patients who undergo bypass, and these data strongly support the conclusion that it can be used as an inotrope for such patients, by injecting or infusing it into such patients after such surgery has been completed.

In control patients, who received a placebo rather than FDP, the baseline value for left ventricular stroke work index (LVSWI) was 27.0±3.09 (i.e., this value was measured on such patients after the start of surgery, but before cardiopulmonary bypass began). When the LVSWI values were measured again, 24 hours after surgery had been completed to correct the inadequate supply of blood to the heart muscle, the LVSWI values had increased to 28.9±2.68. Accordingly, the increment (on average) was 1.9.

In patients who received FDP, the baseline values for LVSWI were 28.9±2.91; this baseline value was not significantly different from the baseline average for the control patients. when LVSWI was measured again, 24 hours after surgery WAS completed, the LVSWI values in these FDP-treated patients increased to 35.75±2.92. The increment between baseline values and post-surgical values was, on average, 6.85 in the FDP-treated patients. This increase in stroke work index was 3.6 times higher than the average increase in control patients who did not receive FDP. The difference between the two groups was statistically significant at a confidence level of well over 95%.

Since LVSWI is a good indicator of total functioning of the left ventricle, the finding of substantially increased LVSWI values, in FDP-treated patients compared to control patients, indicates that the FDP did indeed act as an inotrope.

As shown in FIG. 1, FDP also helped to reduce unwanted elevations in "pulmonary artery wedge pressures" (PAWP) after bypass surgery, compared to a placebo. In control (placebo) patients, baseline PAWP values before surgery were 11.67±1.1. By 24 hours after surgery, those PAWP values had decreased to 8.67±1.57; the average decrease was 3.0. By contrast, in FDP-treated patients, the baseline PAWP values were 10.13±1.42 (not statistically different from the control values By 24 hours after surgery, those PAWP values had decreased to 5.13±0.69. On average, the drop in PAWP values were 6.0, which was twice as much as the drop in PAWP values in control patients.

These data, shown graphically in FIG. 1, clearly indicate that in patients who underwent surgery involving cardiopulmonary bypass, FDP had a completely beneficial inotropic effect.

Formulations and Dosages

It has been discovered by the Applicant company (Cypros Pharmaceutical Corporation) that FDP can be lyophilized in a pure and chemically stable form which contains a surprisingly high residual moisture content, in the range of about 12 to about 16% residual water, by weight. By contrast, most lyophilized products contain less than about 2% residual water. Such lyophilization can be carried out in a completely sterile manufacturing process, which provides pure, sterile, stable FDP in a powder or cake form, in a sealed vial containing up to about 5 grams of FDP. The powder or cake is stable for months or even years when stored at room temperature, and it is ideally suited to reconstitution for injection, using water or any other injectable aqueous solution, such as a dextrose solution, Ringer's lactate, etc. Accordingly, since FDP itself in an aqueous solution is relatively unstable and will spontaneously hydrolyze and lose one or both of its phosphate groups to form inactive and useless byproducts, the use of such "partially lyophilized" preparations of FDP is regarded as the best mode of carrying out this invention.

Any suitable (i.e., pharmacologically acceptable) salt of FDP can be used, such as a sodium salt, or divalent salts such as calcium or magnesium salts, or mixtures thereof. In general, potassium salts should not be administered intravenously, since an abrupt infusion of potassium might interfere with cardiac functioning. In the quantities that are relevant herein, the amount of sodium contained in the sodium salt of FDP will not have any adverse effects on the large majority of people who are likely to need it. However, if sodium causes serious concern in a specific patient, the patient can be treated with a diuretic drug to increase the elimination of sodium in urine or feces.

Isomers of FDP other than fructose-1,6-diphosphate cannot be used. Although certain other isomers (including naturally fructose-2,6-diphosphate) occur naturally in mammalian cells, they serve other purposes and are not created or consumed as intermediates in the glycolysis pathway.

Preferred dosages for bolus injection or intravenous infusion of FDP will generally be in the range of about 75 to about 400 mg/kg (i.e., milligrams of FDP per kilogram of patient body weight). If intravenous infusion is used, preferred infusion rates will typically be in the range of about 0.5 to about 5 mg/kg/minute.

EXAMPLES

Example 1

Effects of FDP in Patients with Elevated LVEDP

The study group described in both Examples 1 and 2 comprised 47 men and women who underwent diagnostic cardiac catheterization at the University of Mississippi Medical Center, in Jackson, Miss. Most patients were known or suspected to have coronary artery disease (CAD). Prior to catheterization, the study was explained to the patients, and they were assured that it would require no longer than 30 minutes, plus the time required to complete the diagnostic procedure. Those who volunteered to participate gave informed consent, and the study protocol was approved by the Institutional Review Board.

Based on pre-treatment LVEDP values, patients were separated into those with normal LVEDP values (less than 12 mm Hg) and elevated LVEDP ($\geq$12 mm Hg); this boundary value is generally considered to be at the lower limits of abnormal. In the impaired group, 3 patients had a resting LVEDP of 12 mm Hg; in all cases, these values rose significantly following the ventriculogram, indicating impaired LV function. Clinical and angiographic data of both groups are shown in Table I.

In the group with LV dysfunction, 14 patients had elevated LVEDP levels (12 mm HG or higher) combined with abnormally low left ventricular stroke work index (LVSWI) values (less than 30 gm-m/m$^2$); this combination is regarded as severe left ventricle dysfunction; such patients are usually at or near a level of impending or active cardiac failure, as distinct from chronic discomfort and lesser levels of dysfunction. The responses of these patients with severe heart dysfunction are not included in Table II; these data are contained in Table IV instead.

All tests were conducted during left and right heart catheterization, usually in the morning after an overnight fast. With a patient in the supine position, a pigtail catheter and a Swan-Ganz thermodilution catheter were introduced via the femoral route. Pressures were recorded with Statham P23Db transducers using an Electronics for Medicine multichannel recorder, VR-12 (Pleasantville, N.Y.). For all pressures, the O reference was set at mid-chest.

Hemodynamic measurements included heart rate (HR, beats/min), mean and phasic systemic arterial pulmonary arterial pressure, LV peak systolic pressure, and end diastolic and mean pressures (all pressures in mm Hg). The cardiac output (CO, L/min) was determined by either thermodilution or the Fick method. From the above measured parameters, systemic and total pulmonary resistance (SVR and TPVR, dynes sec$^{-5}$), stroke volume (SV, ml/beat), stroke volume index (SVI, ml/beat/m$^{-2}$), and LV stroke work index (LVSWI, gm.m.m$^2$) were calculated according to the methods described in Grossman et al 1991.

Baseline hemodynamic measurements were obtained. A sodium salt of FDP (sold under the trademark "Esafosfina" by Biomedica Foscama, Rome, Italy) was then dissolved in sterile pyrogen free water to form a 10% (w/v) solution, which was infused over 7 to 14 minutes into a central vein.

At the beginning of the study, a number of subjects received approximately 70 to 75 mg/kg of FDP (i.e., milligrams of FDP per kilogram of body weight). This was the same dose that had previously been tested in a safety study involving healthy volunteers. In that study, FDP at 75 mg/kg significantly increased the respiratory quotient (RQ) and calories derived from carbohydrates, indicating increased glycolytic activity.

Since no adverse effects were observed in the low-dosage tests on patients with coronary artery disease, the remainder of the patients received 150 mg/kg. In the group with diminished LV function, 14 patients were infused with approximately 75 mg/kg, while the other 16 received 150 mg/kg. In the group with normal LVEDP, 14 subjects received 70 to 75 mg/kg, and 3 received 150 mg/kg.

Measurements of all hemodynamic parameters were performed at 10, 15 and 20 minutes after the termination of FDP infusion. Cardiac output determinations were made at 15 and 20 min post-infusion. Thereafter, the diagnostic procedure was carried out in a routine manner that included coronary arteriogram and ventriculogram.

Measurements made following FDP administration were compared with baseline values before administration, employing Student's t-test for paired observations. The differences were considered significant only when the two-tailed P value was less than 0.05. Differences in hemodynamic values between the two dosages of FDP (75 mg/kg and 150 mg/kg) were compared using two-tailed t-test for unpaired observations. Relations of changes in LVEDP to changes in LVSWI, and those induced by the two different doses of FDP, were analyzed using linear regression analysis. Significance of data was determined at the level of probability P less than 0.05. For the statistical analysis, the values in the text and tables indicate mean values plus or minus the standard error of the mean.

As shown in Table I, baseline demographic and angiographic characteristics were similar between the groups with elevated LVEDP, and normal LVEDP. Of the 30 patients with elevated LVEDP, three patients had no angiographic evidence of CAD, although two of them had previous myocardial infarction (MI), and one was in heart failure. In the subset with LVSWI values less than 30 g-m/m$^2$, six patients had previous MI, five had triple-vessel disease, two had two-vessel disease, and one had mitral regurgitation.

As shown in Table II, in patients with depressed LV function, administration of FDP resulted in a slight reduction in the heart rate from 78 beats/min to 75 beats/min (NS), with no significant changes in the LV systolic and mean arterial pressures. There was a significant reduction in LVEDP, from 22±1.3 mm Hg to 16.73±1.46 mm Hg ($P<0.0001$). FDP afforded a significant increase in SV, from 62.5±3.63 ml to 73.3±4.49 ml ($P<0.0001$). The pulmonary hemodynamics were also affected by FDP, as evidenced by the significant decrease in mean pulmonary artery pressure (MPAP) ($P<0.002$, Table I). The SVR diminished from 1667±92 to 1510±89 (dynes-sec/cm$^5$; $P<0.001$) by virtue of increased CO ($P<0.0001$) and unaltered arterial pressures (Table II).

As stated above, 14 of the patients with elevated LVEDP were infused with approximately 75 mg/kg, while the other 16 were infised with 150 mg/kg. In comparing the hemodynamic responses between the two dosages of FDP, there were differences in several parameters. There was no significant change in the HR with 150 mg/kg, but the 75 mg/kg dosage induced a moderate decline in the HR ($P<0.001$). The baseline LVEDP in those patients infused with 150 mg/kg was 24±2.06 mm Hg, whereas in the 75 mg/kg group it was 19.7+2.36 mm Hg. After FDP treatment with 150 mg/kg, the LVEDP declined from 24 to 19.7±1.36 mm Hg; in those patients receiving 75 mg/kg, it diminished from 19.7 to 13.4±1.1; mm Hg. Similarly, the decline in PVR was more pronounced in the 75 mg/kg group. In both instances, the differences were significant ($P<0.05$).

It might appear that in some respects, the lower dosage of FDP had a more pronounced effect on LV function. However, it is believed by the Inventor herein that this was a chance result, due to the fact that patients receiving 150 mg/kg tended to have more depressed LV function. The changes in LVEDP and LVSWI induced by 150 mg/kg showed a strong correlation (r=0.77; $P<0.001$), whereas no correlation was found for those parameters in patients receiving 75 mg/kg.

Example 2

Effect of FDP in Patients with Normal LVEDP

As noted above, 17 of the patients who had coronary artery disease and who were undergoing diagnostic cardiac catheterization had LVEDP values that were considered to be in the normal range (i.e., less than 12 mm Hg). Baseline LV end diastolic pressures in these patients ranged from 1 to 10 mm Hg (mean 5.53±0.60 mm Hg). These patients had a mean CI value of 2.44±0.094 min/m$^2$, which is at the lower limits of normal.

As indicated by the data in Table III, FDP infusion generally produced similar but less pronounced hemodynamic changes, compared to the effects in the group with LV dysfunction; however, FDP did not alter the LVEDP and MPAP values in the patients with normal beginning LVEDP values. There was a slight but significant decline in HR ($P<0.001$) and no change in aortic and ventricular pressures. FDP treatment resulted in a small but significant increase in CO ($P<0.05$), CI ($P<0.04$), SVI ($P<0.001$), and LVSWI ($P<0.002$). There was a 12% decline in PVR ($P<0.004$).

Example 3

Effects of FDP in Patients with Elevated LVEDP Combined with Low LVSWI

Fourteen patients who suffered from elevated LVEDP levels also suffered from diminished left ventricular stroke work index (LVSWI) values (less than 30 gm-m/m$^2$). These patients had the most severely compromised LV function, and the data from their responses to FDP were compiled separately. These data are provided in Table IV.

The hemodynamic responses indicate that FDP exerted a direct inotropic effect on the heart; CO, CI, SVI, LVSWI values all increased significantly, while LVEDP values decreased significantly; however, there was no significant change in heartbeat rate. Systemic and pulmonary resistances also declined moderately, due to increased cardiac output (CO) combined with unchanged aortic and pulmonary pressures.

One patient had mitral regurgitation and was in heart failure. With FDP treatment, her LVEDP declined from 22 to 14 mm Hg, and her CI increased.

Example 4

Effects of FDP in CABG Patients who Underwent Cardiopulmonary Bypass Surgery

All surgical and testing procedures described in this example were carried out at the Harefield Hospital, in Harefield, England, under the supervision of a qualified cardiac anesthesiologist. These tests were initiated and sponsored by Cypros Pharmaceutical Corporation, which obtained approval from the United States Food and Drug Administration prior to carrying out these Phase II human clinical trials, so that the data gathered in these tests could subsequently be used in a United States drug approval application. Phase I trial requirements (to establish baseline values for FDP using tests on healthy volunteers) were waived, for these surgical tests, by the U.S.F.D.A., since FDP is a naturally occurring biochemical that occurs only as a short-lived intermediate which is quickly consumed during glycolysis.

Twenty patients were selected for coronary artery bypass graft surgery, usually based on complaints of chest pain or evidence of myocardial infarction. These patients underwent routine screening and evaluation to determine that their coronary artery occlusions were severe enough to warrant artery grafting rather than balloon angioplasty or other less-invasive procedures.

Anesthesia was induced by standard techniques, using inhalation agents, injectable agents, or both, as determined for each patient by a skilled anesthesiologist. There were no significant differences in anesthesia methods between the FDP treatment group and the untreated control group.

Throughout surgery, anesthesia was maintained with a combination of agents that sustained unconsciousness, paralysis, and immobility; this required the use of a mechanical ventilator before cardiac bypass began and after it ended. Patients were monitored with various instruments either situated externally (e.g., to analyze exhaled gases), upon the surface of their body (e.g., a stethoscope and EKG recording electrodes), or within their body, through a normal orifice (such as a temperature probe placed in the esophagus) or by insertion through the skin (e.g., pressure recording catheters were passed through an incision in the groin or neck, and advanced into the chambers of the heart or a pulmonary artery).

The chest was opened by longitudinal incision over and through the sternal bone. The chest wall was spread open and held apart with a chest retractor (also called an "alligator" in England).

If the arterial graft was taken from the leg (this occurred in twelve of the twenty patients; mammary artery coupling was used in the remaining 8 cases, with no statistically significant differences between treatment and control groups), an additional dissection was made along the length of the patient's leg, on a side that had not previously had its veins stripped for cosmetic purposes or for the treatment of varicose veins. A segment of saphenous vein was removed, and identified at its distal end (which became the proximal end when arranged across the heart). Any branches of the vein were carefully sutured shut, to make sure it was watertight except for the normal orifices at each end.

An infusion of 250 mg/kg of a stable formulation of a suitable sodium salt of FDP was used. This salt mixture contained a ¾ saturation level of sodium (i.e., there were enough sodium ions present in the solution to bond ionically to ¾ of the four acidic groups on each molecule of FDP, while the pH was sufficiently low that the remaining ¼ of the organic acid groups remained non-ionized). This FDP salt was injected into a peripheral vein, beginning up to about 30 minutes before the start of circulatory bypass using a heart-lung machine. This infusion was diluted into a larger volume (usually about 250 to 450 milliliters) of a compatible, sterile intravenous infusion fluid, such as 0.9% saline solution.

A matched saline placebo was injected into patients in the control population. The anesthesiologist(s) working on any specific patient were unaware whether they had infused that patient with FDP or a placebo.

The bypass machine was prepared by filling the pumping chamber with either blood or an oxygenated solution compatible with blood; this process is known as pump priming. The aorta was clamped, punctured, and received the effluent hose from the bypass machine. The right atrium, or one of the large venous vessels leading to it, was punctured and received the hose which carried deoxygenated blood to the bypass machine. Additional cannulas were inserted into the coronary arteries and the coronary (venous) sinus, to allow independent perfusion of the heart muscle with cold "cardioplegia" solution containing high concentrations of potassium, to cause the heart to stop beating during surgery. In most cases, additional hoses from the bypass machine were inserted into one or more pulmonary arteries and veins, to allow separate perfusion of a patient's lungs. Once bypass was established, the patient's entire body and brain (excluding his/her heart) received all needed oxygen and nutrients by additions to the blood circulating outside his or her body, through the bypass machine. The patient's heart, however, was being perfused only by the cardioplegia solution, and was suffering the ischemic insult that necessarily accompanies this type of surgery.

The saphenous vein segment or mammary artery end was sutured into place on the surface of the heart, to create a new coronary artery passageway which circumvented and bypassed an obstructed native coronary artery. After suturing and pressure testing were completed, the heartbeat was restarted, usually with the aid of electric shock, which was often needed more than once due to the tendency of hearts to fibrillate as they are rewarmed and restarted after surgery. The hoses from the bypass machine were slowly clamped off, to test whether the patient's heart could regain adequate blood pumping pressure, and to allow continuing inspection for leakage from the sutured artery grafts. If all was well, the bypass hoses were removed from the aorta and right side of the heart, and their entry punctures were sutured shut. The basin formed by the pericardial membrane was again inspected for leakage, and plastic drainage tubes were inserted into the pericardial space and secured in position with dissolving sutures; these tubes passed through the skin at a location other than the site of the incision. The alligator jaws were closed and removed, and the divided sternal bone was wired shut using steel wire loops. The skin and soft tissues were closed, and the patient was returned to an intensive care unit with mechanical ventilator still operating, and various drains and intravenous cannulae in place.

After a period of recovery (usually several hours, depending on the condition of the patient), the mechanical ventilator was removed and the patient breathed on his/her own. Other interventions and monitors were withdrawn gradually, usually over a period of several days, as the patient regained strength and returned to an independent state.

Post-operative monitoring included EKG recording, CK enzyme concentrations in circulating blood, and measurements of heart function through invasive pressure monitoring catheters and echocardiography.

When FDP-pretreated patient populations were compared to untreated control populations, these measurements clearly demonstrated that injection of FDP, before cardiopulmonary bypass began, resulted in both (1) substantial reductions of heart cell damage (as measured by CK release into blood by ruptured cells), and (2) substantial reductions in the hemodynamic abnormalities and other manifestations of stress that are shown by hearts that have undergone bypass operations.

These results are shown graphically in FIGS. 1–3. In these drawings, references to "AUC" refer to "area under the curve". These data points, calculated individually for each patient based on the data points measured for that patient over a span of several days, provide an overall numerical indication of how much total stress and damage a patient suffered, as measured by CK blood levels and elevated PAWP values which lasted for several days.

These data, combined with the other data provided herein, support the assertion that FDP can act as a useful and helpful inotrope drug in patients who have undergone cardiopulmonary bypass surgery, such as coronary artery bypass surgery.

Thus, there has been shown and described a new and useful means for treating patients who have undergone cardiopulmonary bypass surgery, and who need to be treated with an inotropic drug to increase the strength of the heartbeat. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Angelos, M. G., et al, "Fructose-1,6-diphosphate fails to limit early myocardial infarction size in a canine model," *Ann. Emerg. Med.* 22: 171–177 (1993)

Brunswick, R., et al, "Preservation of myocardium by infusion of fructose diphosphate following coronary occlusion," *Am J Cardiol* 49: 1008 (1982)

Cargnoni, A., et al, "Role of timing of administration in the cardioprotective effect of fructose-1,6-bisphosphate," *Cardiovasc Drugs Ther* 6: 209–17 (1992)

Eddy, L. J., et al, "Lack of a direct metabolic effect of fructose, 1,6-diphosphate in ischemic myocardium," *Am J Physiol* 241: H576–83 (1995)

Farias, L. A., et al, "Effects of fructose-1,6-diphosphate, glucose and saline on cardiac resuscitation," *Anesthesiology* 65: 595–601 (1986) Galzigna, L., et al, "Some effects of FDP on rat myocardial tissue relate to a membrane stabilizing action," *Cell Biochem. Function* 7: 91–96 (1989)

Grandi, A. M., et al, "Improved left ventricular function after short-term treatment with fructose-1,6-diphosphate," *Clin Ther* 10: 372–80 (1988)

Grossman, W., "Evaluation of systolic and diastolic function of the myocardium," pages 319–39 in Grossman and Baim, eds., *Cardiac Catheterization and Angiography and Intervention* (Lea & Febiger, Philadelphia, 1991)

Hassinen, I. E., et al, "Mechanism of the effect of exogenous fructose 1,6-bisphosphate on myocardial energy metabolism," Circulation 83: 584–93 (1991)

Janz, T. G., et al, "The effects of fructose-1,6-diphosphate on myocardial damage in acute coronary artery occlusion," *Resuscitation* 22: 45–54 (1991)

Lazzarino G., et al, "Protective effects of exogenously administered fructose-1,6-diphosphate from ischemia reperfusion damage induced on isolated rat heart," *Ital J Biochem* 38: 251A–253A (1989)

Lazzarino, G., et al, "Ischemia and reperfusion: effect of fructose-1,6-bisphosphate," *Free Radic Res Commun* 16: 325–39 (1992)

Marchionni, N., et al, "Hemodynamic and electrocardiographic effects of fructose-1,6-diphosphate in acute myocardial infarction," *Am J Cardiol* 56: 266–269 (1985)

Marchionni, N., et al, "Improved exercise tolerance by i.v. fructose-1,6-diphosphate in chronic, stable angina pectoris," *J Clin Pharmacol* 28: 807–11 (1988)

Markov, A. K., et al, "Hemodynamic, electrocardiographic, and metabolic effects of fructose diphosphate on acute myocardial ischemia," *Am Heart J* 100: 639–46 (1980)

Markov, A. K., "Hemodynamics and metabolic effects of fructose 1–6 diphosphate in ischemia and shock—experimental and clinical observations," *Ann Emerg Med* 15: 1470–7 (1986)

Markov, A. K., et al, "Increasing survival of dogs subjected to hemorrhagic shock by administration of fructose 1–6 diphosphate," *Surgery* 102: 515–27 (1987)

Munger, M. A., et al, "Effect of intravenous fructose-1, 6-diphosphate on myocardial contractility in patients with left ventricular dysfunction," *Pharmacotherapy* 14: 522–8 (1994)

Pasque, M. K., et a, "Metabolic intervention to affect myocardial recovery following ischemia," *Annals of Surgery* 200: 1–12 (1984)

Tortosa, A., et al, "Fructose-1,6-bisphosphate fails to ameliorate delayed neuronal death in the CA1 area after transient forebrain ischaemia in gerbils, "*Neuropharmacology* 32: 1367–71 (1992)

Zhang, J. N., et al, "Protective effect of exogenous fructose-1,6-diphosphate in cardiogenic shock," *Cardiovasc Res* 22: 927–32 (1988)

We claim:

1. A method of increasing cardiac pumping output in a human patient who has undergone cardiopulmonary bypass surgery and who is in need of drug treatment to increase cardiac pumping output, comprising the following steps:

a. completing a surgical procedure involving cardiopulmonary bypass on the patient; and, b. intravenously injecting into the patient, after the surgical procedure involving cardiopulmonary bypass has been completed, an injectable liquid containing fructose-1,6-diphosphate in a therapeutically effective dosage which increases cardiac pumping output and which does not cause an increase in heartbeat rate.

2. The method of claim 1, wherein the fructose-1,6-diphosphate is administered as a sole inotropic drug.

3. The method of claim 1, wherein the fructose-1,6-diphosphate is co-administered along with a quantity of a second inotropic drug, wherein the fructose-1,6-diphosphate reduces the quantity of the second inotropic drug which is required to achieve a desired inotropic effect in the patient being treated.

4. The method of claim 3, wherein the second inotropic drug is selected from the group consisting of digitalis glycosides, inotropic catecholamines, and amrinone lactate.

5. The method of claim 1 wherein the fructose-1,6-diphosphate is intravenously injected by means of continuous intravenous infusion.

6. The method of claim 1 wherein the fructose-1,6-diphosphate is administered to a patient in a dosage range of about 75 milligrams to about 400 milligrams of fructose-1, 6-diphosphate per kilogram of patient body weight.

* * * * *